United States Patent [19]

Griffin et al.

[11] Patent Number: 4,901,734
[45] Date of Patent: Feb. 20, 1990

[54] DUAL-THERMISTOR THERMODILUTION CATHETER

[75] Inventors: Joseph C. Griffin, Atco; James L. Skaggs, Indian Mills, both of N.J.

[73] Assignee: Nova Medical Specialties, Indian Mills, N.J.

[21] Appl. No.: 214,002

[22] Filed: Jun. 30, 1988

Related U.S. Application Data

[63] Continuation-in-part of Ser. No. 85,552, Aug. 17, 1987, abandoned.

[51] Int. Cl.⁴ .................................................. A61B 5/02
[52] U.S. Cl. .................................... 128/692; 128/713; 128/736
[58] Field of Search .............................. 128/691–692, 128/694, 736, 713; 73/204.25

[56] References Cited

U.S. PATENT DOCUMENTS

| | | | |
|---|---|---|---|
| 3,595,079 | 7/1971 | Grahn | 128/692 X |
| 4,329,993 | 5/1982 | Lieber et al. | 128/691 X |
| 4,476,877 | 10/1984 | Barker | 128/736 |
| 4,632,125 | 12/1986 | Webler et al. | 128/692 |
| 4,676,252 | 6/1987 | Trautman et al. | 128/671 |
| 4,685,470 | 8/1987 | Sekii et al. | 128/692 |
| 4,730,623 | 3/1988 | Lee | 128/692 |

Primary Examiner—Angela D. Sykes
Attorney, Agent, or Firm—Shoemaker and Mattare, Ltd.

[57] ABSTRACT

An apparatus for reporting accurate results in thermodilution by single pulmonary arterial catheterization procedures comprises an elongated multilumen catheter having a distally-placed thermistor and proximally-placed thermistor and a plurality of electrical sensing means connected to the thermistors. The proximal thermistor is so positioned as to be substantially totally immersed in the blood-injectate mixture to rapidly and accurately determine the temperature thereof. The use of two thermistors so placed provides highly accurate temperature data requiring substantially no correction.

6 Claims, 5 Drawing Sheets

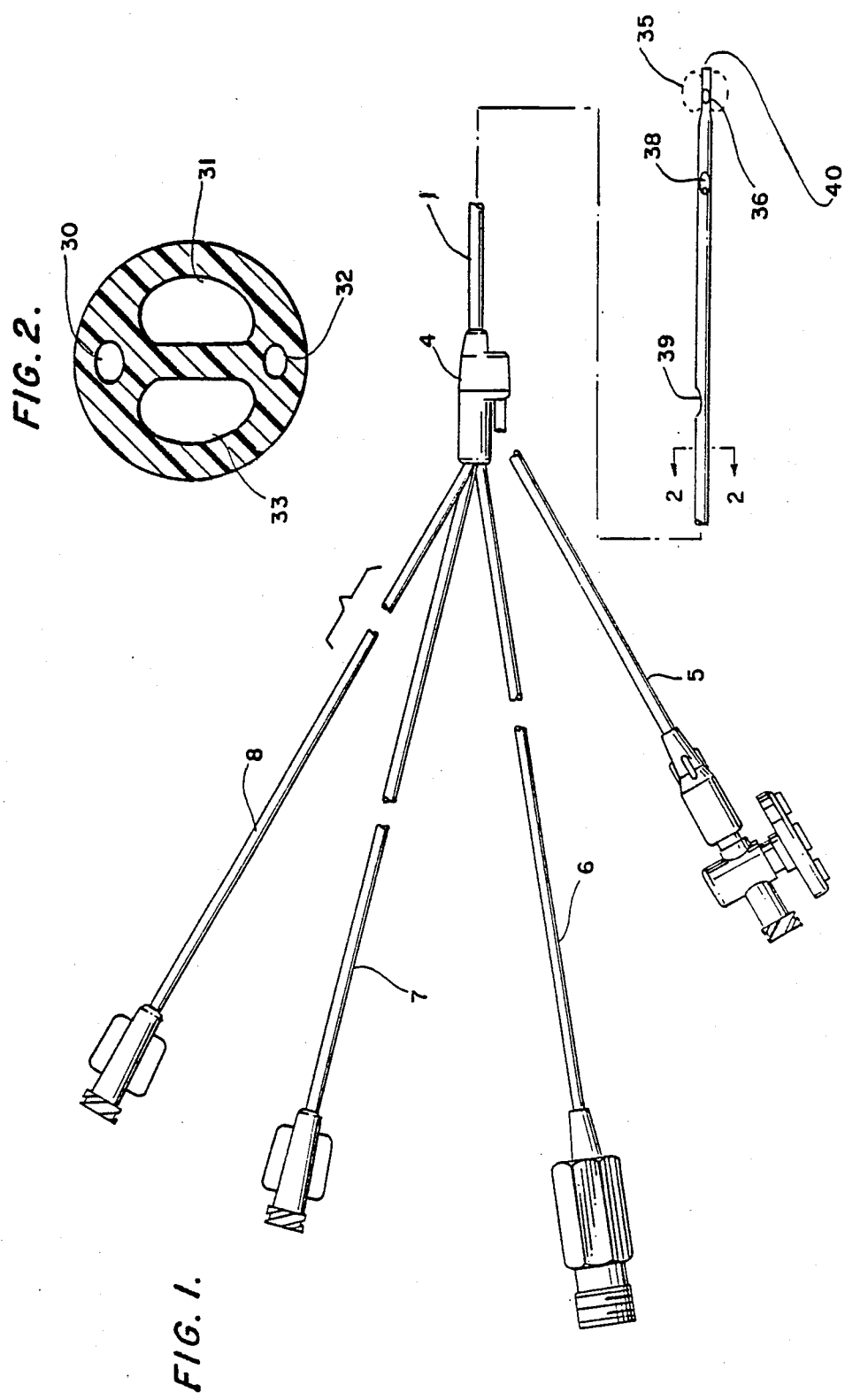

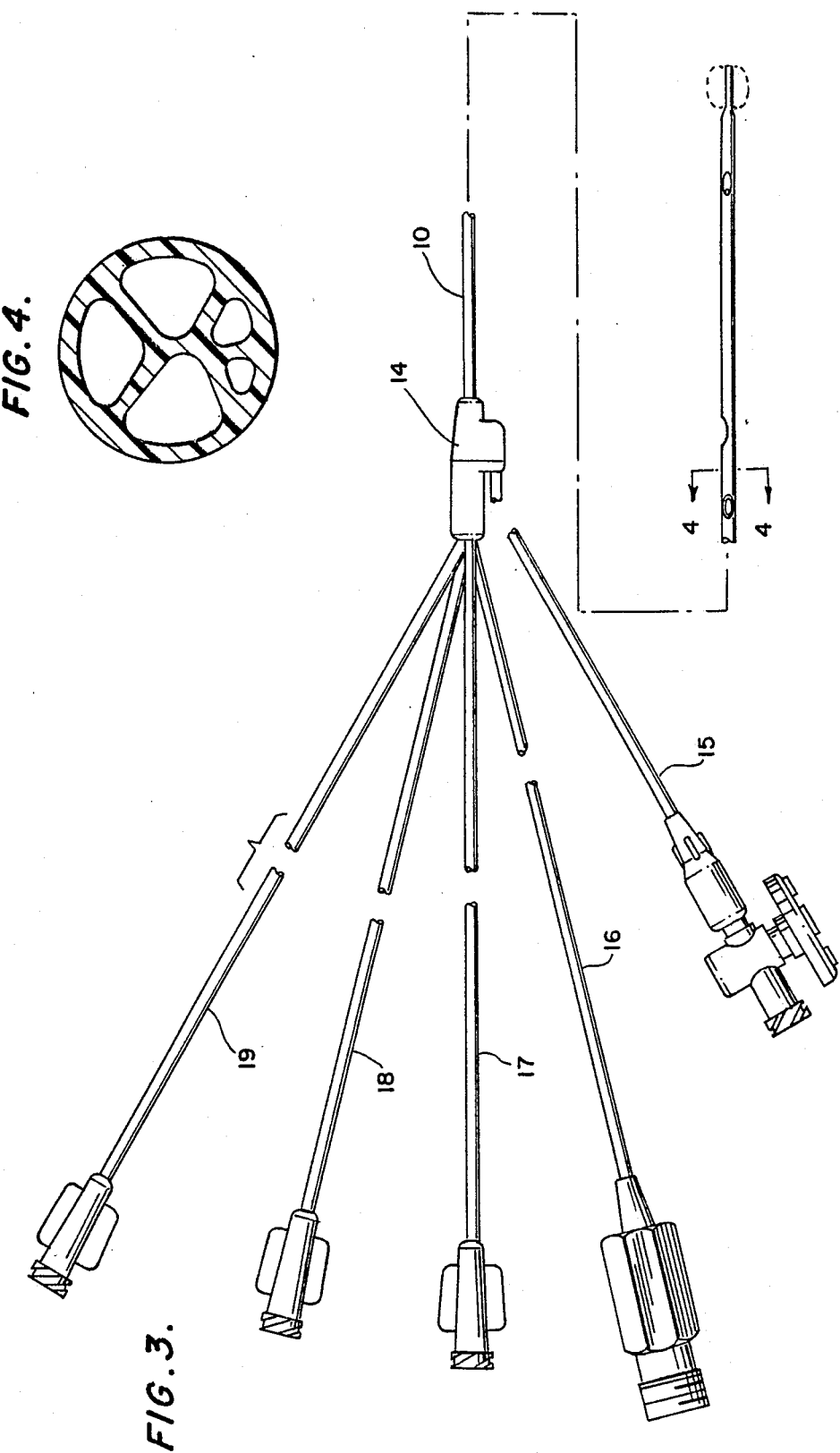

4,901,734

DUAL-THERMISTOR THERMODILUTION CATHETER

BACKGROUND OF THE INVENTION

This is a continuation-in-part application of Ser. No. 85,552, filed Aug. 17, 1987, now abandoned.

The present invention relates to balloon catheters and particularly to balloon catheters that are used for thermodilution studies for providing diagnostic information from the temperature measurements to obtain the quantity of blood flow and the cardiac output.

Thermodilution catheters have been provided for the measurement of the temperature of mixed fluids in the heart and veins in order to provide important diagnostic information. Exemplary of the patent art relating to such catheters is the patent to Hassan H. Khalil U.S. Pat. No. 4,217,910 and the patents and literature references referred to therein.

Thermodilution is an application of the calorimetric principle that, in a mixture of fluids at different temperatures, the heat lost by one fluid equals the heat gained by the other. For each fluid, the mathematical product of the temperature change, specific heat and mass is equal.

The recognized method for the study of blood circulation involves producing a temperature change in the blood at one point in the blood flow and measuring the temperature change at a second downstream point. Assuming that the measurement of the temperature change occurs at a point downstream of the heat source and that the blood's heat content is uniform, the measured change will reflect the amount of blood passing through the blood vessel.

In thermodilution studies heat is either removed from or added to the blood stream. One technique involves the injection of a cooler saline solution or bolus into the blood. In use, a known amount of a cold solution at a known temperature is injected into the right atrium or superior vena cava and the resultant temperature of the blood-bolus mixture is detected by a thermistor while the catheter is placed so that the thermistor bead is in the pulmonary artery. Cardiac output is inversely proportional to the integral of the observed temperature change. The accuracy of this method is dependent upon the accuracy of the measurement of the temperature of the injectate and the accuracy of the measured temperature of the resultant blood-injectate mixture. Assuming that the blood's heat content is uniform, the measured change in temperature provides a means of calculating the mass of the blood moving in a specific period of time and therefore the amount of blood flowing through the vessel which is a measure of the cardiac output of a particular patient.

The current methods and systems for conducting thermodilution measurements typically utilize external injectate bath temperature probes or external in line temperature sensors for measuring injection bolus temperature. These approaches immediately introduce an error in the calculations due to the fact that there will be some heat exchange and a change in temperature of the fluid in the bolus as it travels into and through the catheter when the catheter is placed in the body.

This condition created a need for an injectate temperature correction factor which could introduce error into the calculation of blood volume or cardiac output.

It is therefore an objective of the present invention to provide a multilumen thermodilution catheter which measures the temperature of the bolus as it is introduced into the blood stream so as to avoid inaccuracies that may occur in calculating cardiac output from the use of a bolus whose temperature is measured external of the body.

SUMMARY OF THE INVENTION

A multilumen thermodilution catheter is described wherein a plurality of temperature sensing means are located adjacent the exterior in the catheter body at different distances laterally from the distal end of the catheter and each of said sensors is individually electrically connected to remote temperature measuring means by individual conducting means which communicate predominately through a single lumen in the catheter body and connecting assemblies, communicating with said lumen, to the remote temperature measuring means. In addition, a thermodilution catheter construction is provided which is unique and provides for a simplified method of construction wherein said catheter comprises an elongate multiple lumen catheter body having a distal end and a proximal end; manifold means located at the proximal end of said catheter body for separately connecting the lumens of said catheter body to sources of fluid, sources of gas and instrumentation and measuring means; a plurality of electrical connection means located in one of said lumens communicating with said instrumentation and measuring means and including at least two temperature sensor means; at least one of said sensor means being connected to at least one of said electrical connection means and being located adjacent the exterior surface of the catheter body near the distal end of said catheter body in a manner so as to be capable of sensing the temperature of fluids adjacent said exterior surface; at least one other of said temperature sensor means being connected to at least one other of said electrical connection means and located proximally of said first sensor means by means of passage of said one other second sensor means and attached electrical connection means from said one lumen containing said plurality of electrical connection means into a second of said lumens at a point adjacent said distally located sensor means and said second sensor means being located at a predetermined locus proximal of said distally located sensor means and affixed in said second lumen in a manner so as to be capable of sensing the temperature of fluid present in said second lumen.

BRIEF DESCRIPTION OF THE DRAWINGS

FIG. 1 is a partially broken plan view of a four lumen thermodilution catheter.

FIG. 2 is a cross-sectional view of the thermodilution catheter of FIG. 1 taken along the lines and arrows 2—2.

FIG. 3 is a partially broken plan view of a five lumen thermodilution catheter provided with an infusion or blood sampling lumen.

FIG. 4 is a cross-sectional view of the thermodilution catheter of FIG. 3 taken along the lines and arrows 4—4.

DETAILED DESCRIPTION OF THE INVENTION

Figure 5:
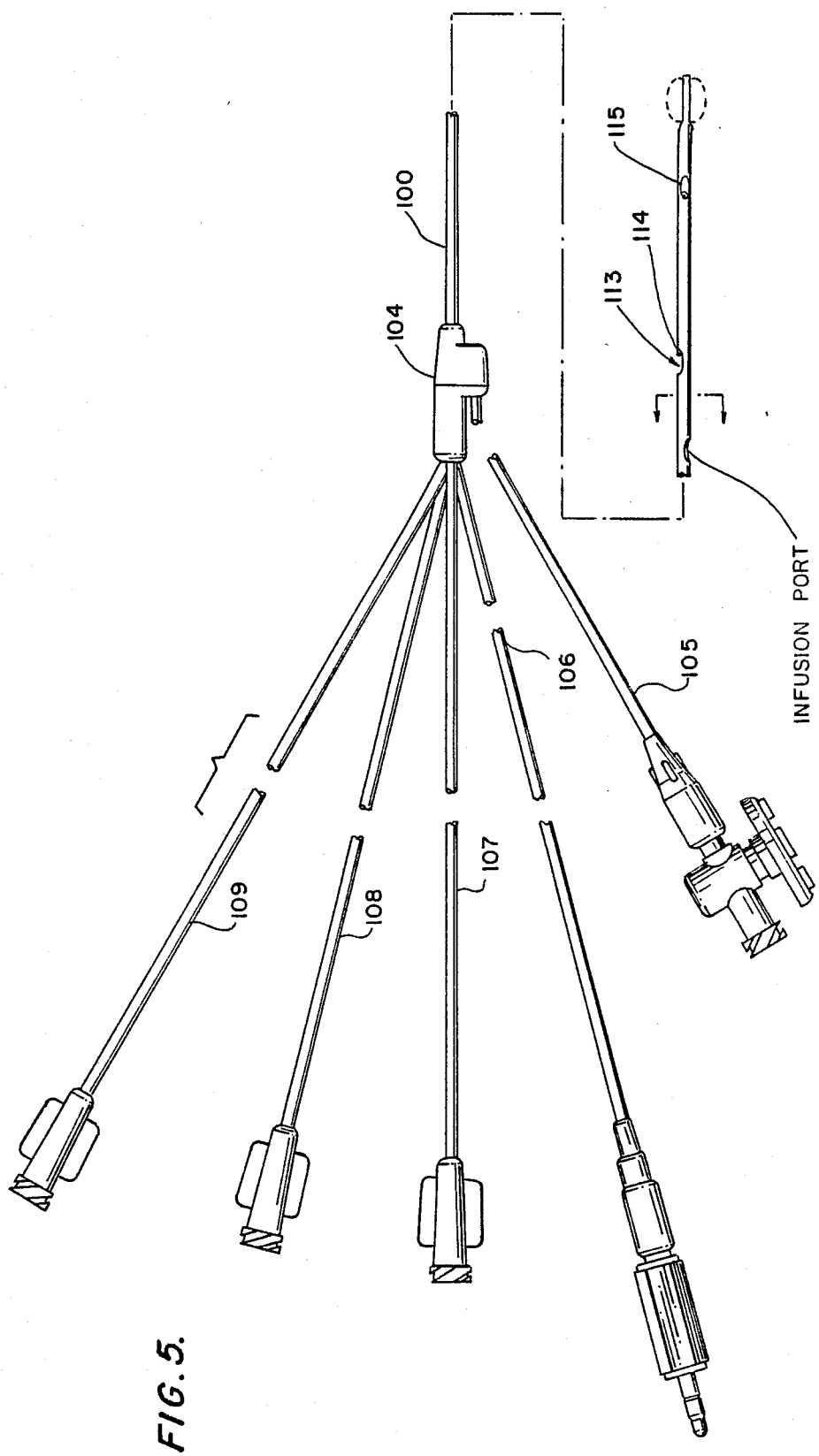
FIG. 5 is a partially broken plan view of another embodiment of a five lumen catheter.

In FIGS. 1, 3 and 5 multilumen catheter bodies 1, 10, and 100 respectively are provided on a balloon catheter. A manifold 4, 14, and 104 are each provided to provide communicating interconnection between the lumens of the catheter body with attachments including gas supply tube and assembly 5, 15, and 105 and thermistor electrical connector and wire containing tubes 6, 16 and 106. Additional lumen connecting assemblies 7 and 8 in FIG. 1; 17, 18 and 19 in FIG. 3 and 107, 108, and 109 in FIG. 5 can be provided for infusion of fluids such as a drug or thermodilution fluids or even blood sampling.

Typically the lumens shown in FIG. 2 provide the following functions. Lumen 32 communicates with gas supply assembly 5 through manifold 4 to inflate and deflate balloon 35 by a means hole 36 in catheter body 1 under the balloon location which communicates with the lumen 32.

Lumen 30 communicates with the electrical connector assembly 6 and is exposed at distal outlet 38 where a thermistor bead is cemented in a manner and location so as to be able to sense temperature at 38 without the lumen being exposed to blood or other fluids in the environment where the catheter is used. The lumen connecting assemblies 7 and 8 communicate with lumens 31 and 33 respectively which lumens independently communicate with the environment outside of catheter by means of openings 39 and 40 respectively. The most proximal of the openings 39 would typically be used for infusion of a bolus at a known fluid both temperature and the change in temperature would be sensed at 38 by the thermistor bead. From the values obtained cardiac output was calculated. The opening 40 to the remaining lumen could be used for the infusion of therapeutic or other fluid or drugs and measure intercardiac blood pressure or even used to withdraw blood samples if desired.

A variation on the foregoing, utilizing a five lumen catheter body, shown in section in FIG. 4 can be used where the additional lumen can be used for a variety of purposes, such as drug therapy, blood sampling and pressure monitoring.

The catheter shown in FIG. 5 provides the improvement of the present invention by maintaining the fluid infusion capability of the five lumen catheter of FIG. 3 while enabling greater accuracy in the measurement in temperature difference between the temperature of the bolus being introduced at opening 113, measured by thermistor bead 114 and the temperature of the blood bolus mixture at thermistor 115.

Referring to FIGS. 6, 7, 8, 9, and 10, it will be more fully appreciated how the dual thermistor catheter of the present invention is constructed.

Figure 6:
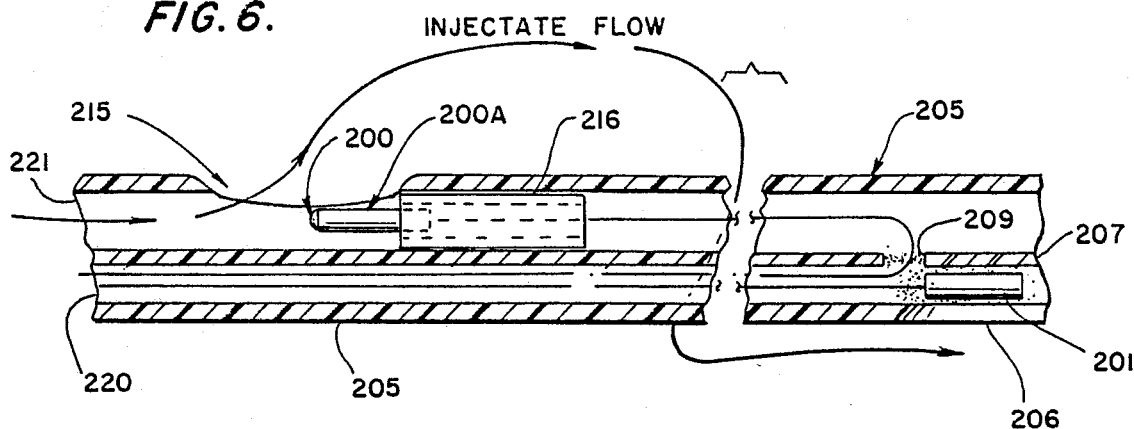
FIG. 6 is a partially broken sectioned view of a portion showing the construction of the thermodilution catheter of the present invention.
Figure 7:
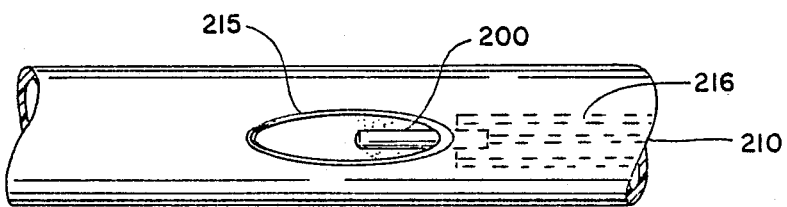
FIG. 7 is a partially broken plan view of some of the details of the construction shown in FIG. 6.
Figure 8:
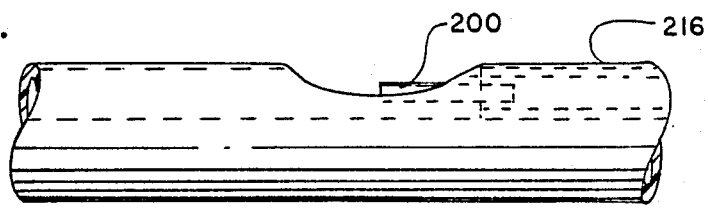
FIG. 8 is partially broken side view of the structure shown in FIG. 7.

In FIG. 6, the thermistor beads are illustrated at 200 and 201. The connecting wires are respectively wire 210 and wire 211.

Both wires 210 and 211 are threaded down a single selected lumen designated 220 toward the proximal end of the catheter. The opening in the catheter wall 205 at 206 is the most distal opening. The lumen wall 207 separating lumen 220 from lumen 221 is provided with an opening 209 through which thermistor bead 200 and thermistor wire 210 are threaded back or distally until thermistor bead 200 is located adjacent the opening 215 which is provided in the exterior wall of lumen 221. During manufacture of the catheter the thermistor bead 200 and wire 210 is fitted with a sleeve 216 which is sized to be received in the lumen 221 in the position shown in FIG. 6. The sleeve 216 is adhesively affixed to the inside of the walls of the lumen 221 so as to provide a fluid tight fit. Placed as described, the lumen 221, proximal of the thermistor bead 200 still communicates with the outside of the catheter body through the opening 215 so that the lumen 221, with the appropriate connections to external fluid transport system can be used for the infusion of a bolus which will travel through the opening 215 and subsequently mix with the fluids, normally blood, external to the catheter. The thermistor bead 200 attached to appropriate instrumentation (not shown) will continuously measure the temperature of the bolus as it is introduced or as it exits the catheter lumen 221.

Referring to FIG. 6, the thermistor bead 200 is preferably housed in a rigid polyamide sleeve 200A. The thermistor bead 200 is fixed inside one end of the rigid sleeve with epoxy resin. The remaining area of the rigid sleeve 200A contains the thermistor conduction wire weld joints and insulation.

Approximately 25% of the insulation side of the rigid sleeve 200A is inserted into a polymer centering tube 216 and bonded to the tube with an appropriate adhesive. The thermistor and centering tube assembly 200, 200A, and 216 are then positioned in the injection lumen 221 to allow the exposed tip of the thermistor bead 200 to be centered in the injection lumen opening 215. Once positioned, the centering tube is also bonded in place with adhesive.

The purpose of positioning the thermistor 200 in this manner is to radially expose 360° of the thermistor into injectate flow as it exits through the proximal port 215. In doing this it is possible to obtain the fastest possible thermo-resistive response time which is in this embodiment on the order of about 0.50 to 0.75 seconds. A thermistor, such as that employed in a conventional thermodilution catheter, which has been embedded into the catheter body or into resin or adhesive at the opening, has a longer response time typically about 1.25 to 1.75 seconds.

Figure 9:
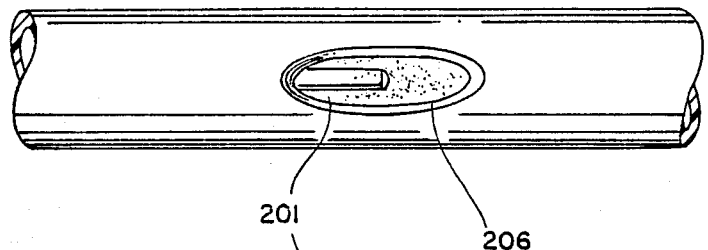
FIG. 9 is a partially broken plan view of another of the details of the construction shown in FIG. 6.
Figure 10:
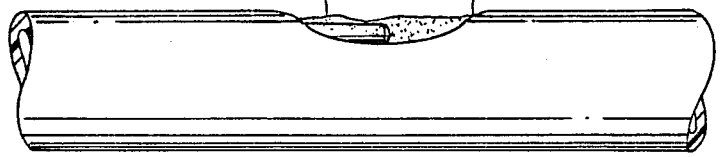
FIG. 10 is a partially broken side view of the structure shown in FIG. 9.
Figure 11:
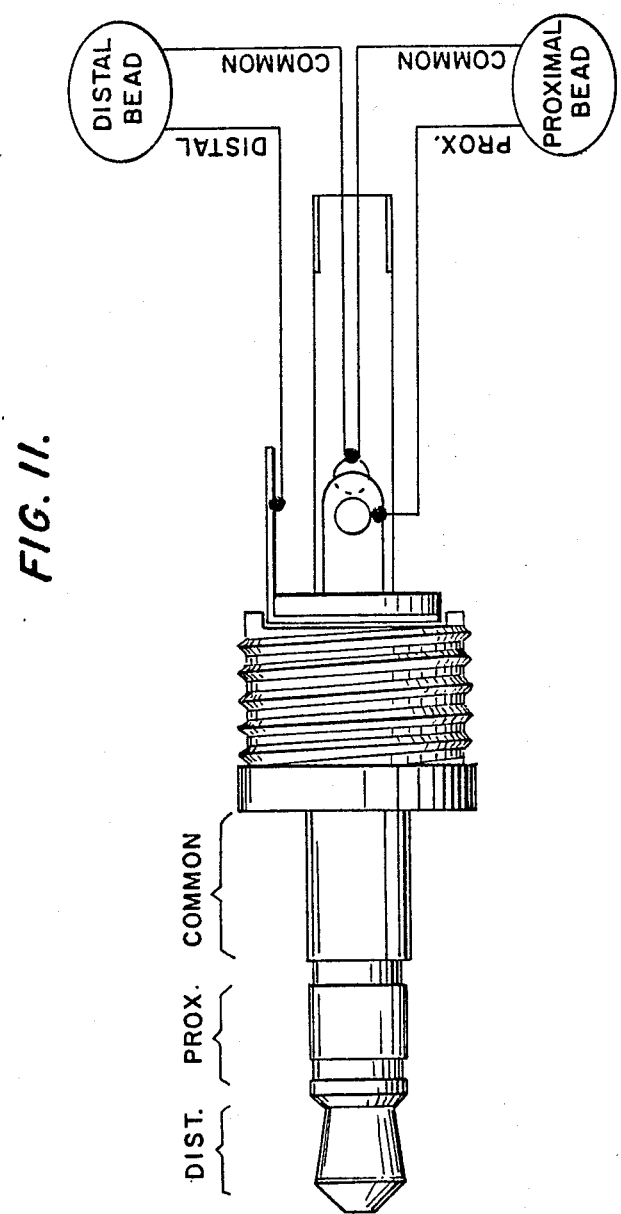
FIG. 11 is a plan view of the electrical connector wiring hook-up to distal and proximal thermistors.

In addition to the faster response time, it is possible to establish a more accurate injectate temperature base line measurement. This structure quickly and accurately measures injectate temperature at the point where it terminates, or leaves, the catheter body. The need for catheter injectate correction factors is eliminated. Since injectate temperature is normally measured outside the patient's body, correction factors must be used to compensate for the heat exchange that takes place when cold injectate is passed through a warm catheter. Correction factors are typically derived as mean valves. The accuracy of a correction factor is dependent upon the influence and consistency of the following variables: catheter raw material density, injectate lumen size, injectate lumen wall thickness, catheter length, depth of catheter insertion into patient, thermal conductivity of fluids or gases contained in adjacent lumens and head exchange from human handling of the syringe containing the iced injectate. The accuracy of the cardiac output measurement obtained through a conventional thermodilution systems can vary as much as 15%. The dual-thermistor catheter of the present invention is capable of reducing this error by at least half. The position and potting of the bead at the distal port (as shown in FIGS. 9&10) is not as critical to the accuracy of the temperature measurement and hence cardiac output.

After placement of the thermistor bead 200, sleeve 216 and wire 210 the opening 209 in lumen wall 207 is sealed with an appropriate material such as urethane or other biocompatible material. The second thermistor bead 201 is then sealed into the position shown in FIGS. 6, 9, and 10 with a biocompatible material.

In operation the bolus fluid and blood mixture with bolus fluid will flow generally in the manner depicted by the lines and arrows shown in FIG. 6. The temperature of the mixed fluids is then measured as before by the thermistor bead 201 and appropriate instrumentation. The temperature difference can then be used to accurately measure the cardiac output through the vessel being studied.

While the foregoing description is of a preferred embodiment of the present invention, it will be appreciated that other embodiments and variations are possible and within the scope of the appended claims which are to be interpreted in the light of the applicable prior art.

What is claimed is:

1. A multilumen catheter for accurate single catheterization thermodilution measurement of cardiac output comprising:
   an elongate multiple lumen catheter body having a distal end and a proximal end;
   manifold means located at the proximal end of said catheter body for separately connecting the lumens of said catheter body to sources of fluid, sources of gas and instrumentation and measuring means;
   a plurality of electrical connection means located in one of said lumens communicating with said instrumentation and measuring means and including at least two thermistors;
   a first one of said thermistors being connected to at least one of said electrical connection means and being located adjacent the exterior surface of the catheter body near the distal end of said catheter body in a manner so as to be capable of sensing the temperature of fluids adjacent said exterior surface;
   at least one other of said thermistors being connected to at least one other of said electrical connection means and located proximally of said first thermistor by means of passage of said one other thermistor and attached electrical connection means from said one lumen containing said plurality of electrical connection means into a second of said lumens at a point adjacent said distally located first thermistor, and said one other thermistor being located at a predetermined locus proximal of said distally located first thermistor and affixed in said second lumen, said one other thermistor accurately sensing the temperature of fluid adapted to be present in said second lumen that is adapted to contact said one other thermistor.

2. The multiple lumen catheter of claim 1 wherein electrical connection means are connected to each said thermistor for electrical attachment to temperature measuring instrumentation, said first thermistor being affixed to said catheter at a point adjacent the exterior surface of the catheter body by means of a biocompatible affixing material and positioned to be substantially completely radially exposed to the injectate.

3. The multiple lumen catheter of claim 2 wherein said multiple lumen catheter body contains an inflatable balloon adjacent the distal end of said catheter body.

4. The multiple lumen balloon catheter of claim 3 wherein said at least one other thermistor is affixed proximal to said distal end of said catheter body in fluid tight relationship with the walls of said second lumen so as to prevent the passage of fluid in said second lumen to any portion of said second lumen distal to the point of affixation and said second lumen communicates with the exterior of said catheter body at a point proximal to said point of affixation whereby fluids infused through said second lumen toward the distal end of said catheter body will pass to the exterior of said catheter body at a locus adjacent to the one other thermistor.

5. The multiple lumen balloon catheter of claim 4 wherein said multiple lumen catheter body contains at least three lumens.

6. The multiple lumen balloon catheter of claim 4 wherein said multiple lumen catheter body contains five lumens.

* * * * *